(12) United States Patent
Manasherov et al.

(10) Patent No.: US 9,597,276 B2
(45) Date of Patent: Mar. 21, 2017

(54) COMPOSITION FOR THE PROPHYLAXIS OF CANDIDIASIS

(71) Applicant: OBSHCHESTVO S OGRANICHENNOJ OTVETSTVENNOST'YU "WDS", Moscow (RU)

(72) Inventors: Tamaz Omarovich Manasherov, Moscow (RU); Svetlana Konstantinovna Matelo, Moskovskaya obl. (RU); Tat'yana Vladimirovna Kupets, Moskovskaya obl. (RU)

(73) Assignee: OBSHCHESTVO S OGRANICHENNOJ OTVETSTVENNOST'YU "WDS", Moscow (RU)

( * ) Notice: Subject to any disclaimer, the term of this patent is extended or adjusted under 35 U.S.C. 154(b) by 0 days.

(21) Appl. No.: 14/729,463

(22) Filed: Jun. 3, 2015

(65) Prior Publication Data
US 2015/0265517 A1    Sep. 24, 2015

Related U.S. Application Data

(62) Division of application No. 13/635,909, filed as application No. PCT/RU2011/000407 on Jun. 9, 2011.

(30) Foreign Application Priority Data

Jul. 8, 2010 (EA) .................................. 201001053

(51) Int. Cl.
| A61Q 11/00 | (2006.01) |
|---|---|
| A61K 31/734 | (2006.01) |
| A61K 8/34 | (2006.01) |
| A61K 8/73 | (2006.01) |
| A61K 9/16 | (2006.01) |
| A61Q 19/00 | (2006.01) |

(52) U.S. Cl.
CPC .............. *A61K 8/733* (2013.01); *A61K 8/345* (2013.01); *A61K 9/1623* (2013.01); *A61Q 11/00* (2013.01); *A61Q 19/00* (2013.01); *A61K 2800/59* (2013.01)

(58) Field of Classification Search
CPC .............. A61K 9/0053; A61K 2300/00; A61K 31/734; A61K 9/1623; A61K 8/733; A61K 8/34; A61Q 11/00
See application file for complete search history.

(56) References Cited

U.S. PATENT DOCUMENTS

| 4,775,525 A * | 10/1988 | Pera ...................... A61K 8/0216 424/54 |
|---|---|---|
| 5,549,885 A | 8/1996 | Torchinsky |
| 6,121,315 A * | 9/2000 | Nair ......................... A61K 8/27 424/49 |
| 6,414,035 B1 * | 7/2002 | Vargas Munita ..... A61K 9/0034 514/724 |
| 6,531,141 B1 * | 3/2003 | Marvel .................... A61K 8/06 424/400 |
| 2003/0072827 A1 * | 4/2003 | Steenbergen ............ A61K 8/64 424/771 |
| 2005/0152931 A1 * | 7/2005 | SaNogueira ............. A61K 8/06 424/401 |
| 2006/0008424 A1 | 1/2006 | MacDonald |
| 2006/0286044 A1 * | 12/2006 | Robinson ............... A61K 8/345 424/49 |
| 2009/0035229 A1 | 2/2009 | Eirew |

FOREIGN PATENT DOCUMENTS

| EP | 0 920 857 A2 | 6/1999 |
|---|---|---|
| EP | 0920857 A1 | 6/1999 |
| EP | 1114637 B1 | 11/2001 |
| EP | 1842544 A2 | 10/2007 |
| JP | 2000-333973 A | 12/2000 |
| JP | 2001-524517 A | 12/2001 |
| JP | 2003 081795 A | 3/2003 |
| JP | 2004-269437 A | 9/2004 |
| JP | 2005 187333 A | 7/2005 |

(Continued)

OTHER PUBLICATIONS

Leepal et al. Effect of xylitol with various concentration and duration on the growth of Candida Albicans (In Vitro study). (2009). Indonesian Journal of Dentistry. vol. 16. pp. 72-76.*
Espacenet English abstract of JP 2000-333973 A.
M.D. Mashkovsky, "Medications", Moscow: Novaya Volna Publishing House, publisher S.B. Divov, 2002, vol. 2, pp. 353,365 with partial English translation.
E. V. Kirillova, et al., "Microbiological monitoring of a condition of a dental biofilm at application of chlorhexidine and xylitol in complex treatment of early childhood caries", Stomatologia Detskogo Vozrasta I Profilaktika, 2, 2009, pp. 86-94.

(Continued)

*Primary Examiner* — Frederick Krass
*Assistant Examiner* — Tracy Liu
(74) *Attorney, Agent, or Firm* — Ladas & Parry LLP

(57) ABSTRACT

The invention solves the problem of the practical realization of an effective prophylactic composition which uses available and safe components and which can be recommended for preventing the growth of candidiasis of the skin and/or mucous membranes in humans in the following risk group: sufferers of diabetes mellitus, people with blood diseases, immune deficiency and other serious pathologies, patents after a course of hormone therapy, antibiotic treatment or chemotherapy, as well as for babies and pregnant women; and for people using tooth implants. The composition for the prophylaxis of candidiasis comprises active components, with the active components used being xylitol in a quantity of 0.3-20.0% by mass and sodium or potassium alginate or a mixture thereof in a quantity of 0.01-2.0% by mass, as well as inert components.

18 Claims, No Drawings

(56) References Cited

FOREIGN PATENT DOCUMENTS

| JP | 2008-303188 A | 12/2008 |
|---|---|---|
| JP | 2009-7292 | 1/2009 |
| JP | 2000-333973 A | 12/2012 |
| NL | 1 018 421 C1 | 1/2003 |
| WO | WO99/27922 A1 | 6/1999 |

OTHER PUBLICATIONS

G. A. Samsygina, et al., "Epidemiology of Infectious Inflammatory and the Role of the Candida Fungi in Newborns", Antibiotki I Khimioterapiya, 1998, No. 8, pp. 23-27 with partial English translation.
E.G. Zelenova, et al., "Oral Microflora: Normality and Pathology Textbook", Nizhny Novgorod, NGMA Publishing House, 2004, p. 121 with partial English translation.
International Search Report for PCT International Application RU2011/000407.
Extended European Search Report for European Application 11803866.0.
Ana Isabel Azcurra et al: "Effect of the high molecular weight chitosan and sodium alginate on Candida albicans hydrophobicity and adhesion to cells", Oral Medicine and Pathology, Apr. 1, 2006, XP055210829.
Dary morya. Zabolevaniya pryamoi kishki: lechenie alginatami. Consilium-Provisorum, vol. 3, No. 4, Oct. 19, 2011, together with English translation.
English translation of Japanese official action mailed Mar. 24, 2015 for Japanese Patent Application 2013-518309.
Silvana Barembaum et al, Efecto de Quitosan y Alginato de Sodio sobre la adherencia de c Albicans Autoctonas a Celulas Epiteliales Bucares. (in Vitro). Med Oral 2003: 8: 188-96. Accepted Mar. 28, 2002.
Khaled H. Abu-Elteen, The influence of dietary carbohydrates on in vitro adherence of four Candida species to human buccla epithelial cells. Microbial Ecology in Health and Disease. 2005: 17: 156-162. Accepted Oct. 17, 2005.
English Translation of Search Report for Chinese Patent Application No. 2011 8002 0407.5.
Instructions dated Jun. 10, 2015, for response to official action in Japanese Patent Application No. 2013-518309.

* cited by examiner

COMPOSITION FOR THE PROPHYLAXIS OF CANDIDIASIS

RELATED APPLICATION INFORMATION

This application is Divisional of copending application Ser. No.13/635,909 filed Sep. 19, 2012, which is a 371 of International Application PCT/RU2011/00407 filed Jun. 9, 2011 and which claims priority from Eurasian Patent Organization (EAPO) Patent Application No. 201001053, flied Jul. 8, 2010, the content of which is incorporated herein by reference.

FIELD OF THE INVENTION

The invention relates to dentistry and perfume industries, and specifically to compositions for the prevention of candidiases of the skin and mucosal surfaces (in the mouth, vagina, and the like) in humans. The composition may be a gel for oral hygiene or for application to the human skin or mucosal surfaces, toothpaste, a cream for application to the skin, or a liquid formulation useful for mouth rinsing or washing the human mucosal surfaces or skin or for application to the skin.

BACKGROUND ART

The antifungal medications currently used for the prevention and treatment of diseases caused by *Candida* yeast fungi (*Candida albicans*) have a broad spectrum of side effects and thereby have limited applicability.

Clotrimazole-containing medications (creams and ointments for topical application, solutions for topical application) are the most common topical medications. Contraindications are as follows: hypersensitivity, pregnancy, and with caution during lactation. For the preventive purpose, nystatin ointment is prescribed for preventing the development of candidiasis during long-term treatment with penicillin drugs and other antibiotics, as well as for weakened and depleted patients. The side effects are allergic reactions. Miconazole is administered topically to patients with fungal infections of the skin and nails, In skin diseases, a small amount of liquid is applied to the affected areas and rubbed in, until it is completely absorbed. Application to the skin causes local irritation, allergic reactions, and skin rash. For the prevention of fungal infections of the oral cavity, oral administration in the form of a gel is prescribed to adults and children. It is recommended not to swallow the gel immediately, but to take it in the mouth as long as possible. Oral miconazole is contraindicated in pregnancy and congenital hepatic dysfunction (see M. D. Mashkovsky, "Medications," Moscow: Novaya Volna Publishing House, S. B. Divov Publisher, 2002, Vol. 2, pp. :353-365).

A pharmaceutical composition is known in the form of mouthwashes, comprising chlorhexidine and glutaraldehyde. This composition is recommended for the prevention and treatment of fungal diseases of the oral cavity caused by *Candida albicans* and in patients suffering from AIDS, cancer, or periodontal diseases (see U.S. Pat. No. 5,549,885 A, IPC A61K 7/16, 1996).

In children that used a gel comprising 0.1% chlorhexidine, however, studies of the oral cavity microflora showed that the detection rate of *Candida albicans* yeast fungi increased from 26.7% to 40.0%. In addition, the contamination of the dental plaque with fungi was observed. This was due to the development of dysbiosis upon the application of chlorhexidine (see E. V. Kirillova., V. N. Tsarev, L. P. Kiselnikova, and V. O. Arteniova, Microbiological Monitoring of the Tooth Biofilm when Chlorhexidine and Xylitol are Used in Complex Therapy of Dental Caries in Children of Early Ages," Stomatologiya Detskogo Vozrasta i Profilaktika, 2, 2009).

An anticandidal prophylactic agent is known for fixing dentures, which comprises xylitol to reduce the formation of plaque on dentures (see JP2000333973 A, IPC A61C 13/23, 2000).

This prior-art prophylactic agent has an insignificant level of antifungal effect. Furthermore, its application is limited only to the oral cavity and only to removable dentures.

DISCLOSURE OF THE INVENTION

The problem to be solved by the invention consists of the embodiment of an efficient prophylactic composition that uses available and safe components and that can be recommended for preventing candidiasis of the skin and/or mucous membranes in people who belong to the group of risk, namely: sufferers of diabetes mellitus; people with blood diseases, immune deficiency, or other serious pathologies; patents subjected to hormone therapy, antibiotic therapy, or chemotherapy; babies and pregnant women; and people using dentures.

The solution of this problem is provided by the composition for the prophylaxis of candidiasis, comprising:
  active agents, in weight percent, namely:
  xylitol in an amount of 0.3-20.0;
  sodium alginate, or potassium alginate, or a mixture thereof in an amount of 0.01-2.0% by weight; and
  inert components.

The composition can be manufactured as a gel, toothpaste, a cosmetic emulsion cream, or as a liquid formulation.

For manufacturing the dosage form as a gel, the prophylactic composition comprises the following inert components, in percent by weight
  moistening component 5-70
  gelling component 0.5-3.0
  surfactant 0.3-3.0
  fragrance 0.05-0.3
  preservative 0.01-0.5
  water up to 100.

For manufacturing the dosage form as toothpaste, the prophylactic composition comprises the following inert components, in percent by weight
  abrasive component 10-30
  moistening component 5-70
  gelling component 0.5-3.0
  anticaries component 0.1-2.5
  surfactant 0.5-3.0
  fragrance 0.3-2.0
  sweetener 0.01-0.3
  water up to 100.

For manufacturing the dosage form as a cosmetic emulsion cream, the prophylactic composition comprises the following inert components, in percent by weight:
  moistening component 0.2-10
  surfactant 0.5-4.0
  emollient 0.5-30
  structuring agent 1.0-3.0
  fragrance 0.01-0.5
  preservative 0.01-0.5
  water up to 100.

For manufacturing the dosage form as a liquid formulation, the prophylactic composition comprises the following inert components, in percent by weight:

moistening component 3.0-70
surfactant 0.5-3.0
fragrance 0.01-0.5
sweetener 0.005-0.2
preservative 0.01-0.5
water up to 100.

In the most preferred embodiment, the prophylactic composition comprises, in percent by weight:
xylitol in an amount of 0.6-18.0; and
sodium alginate, or potassium alginate, or a mixture thereof in an amount of 0.1-1.6.

The moistening component useful in preparing the prophylactic composition can be one or more of substances selected from the group containing: sorbitol, glycerol, polyethylene glycol, and propylene glycol.

For preparing the prophylactic composition in the form of toothpaste, the useful abrasive component can be one or more of substances selected from the group containing: silica, polymethacrylate, calcium pyrophosphate, and sodium bicarbonate.

The gelling component useful for preparing the prophylactic composition in the form of a gel or toothpaste can be one or more of substances selected from the group containing hydroxyethylcellulose, xanthan gum, guar gum, and carboxymethylcellulose.

The surfactant useful in preparing the prophylactic composition in any of the above-listed dosage forms can be one or more of substances selected from the group containing: sodium lauryl sulfate, sodium lauryl sarcosinate, glyceryl stearate citrate, glyceryl oleate citrate, potassium cetyl phosphate, cetearyl alcohol, glyceryl monostearate, hydrogenated castor oil, polysorbate 20, cetearyl glycoside, sorbitan isostearate, and alkylamidobetain.

The emollient useful for preparing the prophylactic composition in the form of a cosmetic emulsion cream can be one or more of substances selected from the group containing: caprylic triglycerides, isopropyl myristate, cetearylethyl hexanoate, olive oil, avocado oil, jojoba oil, Shea Butter, wheat germ oil, sunflower seed oil, dimethicone, and cyclomethicone.

The structuring agent useful for preparing the prophylactic composition in the form of a cosmetic emulsion cream can be one or more of substances selected from the group containing: C14-16 fatty alcohols, stearic acid, and palmitic acid.

The anticaries component useful for preparing the prophylactic composition in the form of toothpaste can be one or more of substances selected from the group containing: sodium fluoride, potassium fluoride, sodium monofluorophosphate, potassium monofluorophosphate, and magnesium glycerophosphate.

The fragrance useful for preparing the prophylactic composition in the form of a gel, toothpaste, a liquid formulation, or a cosmetic emulsion cream can be one or more of substances selected from the group containing:
essential oils derived from peppermint, spearmint, sage, eucalyptus, thyme, clove, wintergreen, anise, orange, mandarin, grapefruit, lemon, bergamot, neroli, lavender, and rose; and
menthol, carvone, anethote, eucalyptol, methyl salicylate, phenoxyethanol, citronellol, geraniol, nerol, limonene, and citral.

The sweetener useful. for preparing the prophylactic composition in the form of toothpaste or a liquid formulation can be one or more of substances selected from the group containing: sodium saccharinate, potassium aspartame, stevioside, and potassium or sodium glycyrrhizate.

The preservative useful in preparing the prophylactic composition in any of the aforementioned dosage forms can be one or more of substances selected from the group containing: methylparaben, propylparaben or sodium salts thereof, sodium benzoate, and potassium sorbate.

Theoretical Rationale for the Efficacy

*Candida albicans* is the most frequent causative agent of candidiasis (in up to 62% of the incidences). The factors favoring the occurrence of candidiasis are as follows: neonatal or elderly age, nutritional deficiency, antibiotics, tumors, HIV infection, chemotherapy, hormone therapy, and wearing of dentures. The manifestation of the disease depends on the condition of the colonized tissue, the virulence factors of Candida, and the severity of the host immune response.

Candidiasis is known to develop in the presence of certain physiological changes in the human body and various pathological states, and as a consequence of adverse effects (such as the use of cytotoxic drugs, antibiotics, or hormones). While mild candidiasis incidences occurring mainly among children have previously been reported, currently severe visceral and generalized forms are much more frequent.

Analysis of data collected over a 20-year observation period (see G. A. Samsygina and G. N. Buslaeva, "Epidemiology of Infectious and Inflammatory Diseases and the Role of Candida Fungi in Newborns," Antibiotiki i Khimioterapiya, 1998, No. 8, pp. 23-27), showed a distinct increase in the incidence rate of neonatal infections caused by Candida fungi. The detection rate of Candida fungi increased by factor of seven in this period. Moreover, mucocutaneous candidiasis amounts up to 28.2% of the incidences of infectious and inflammatory diseases of the skin and mucous membranes in newborns. None of the other microbial species feature such a distinct dynamics. This is probably due to the unjustified wide use of antibiotics, especially broad-spectrum semisynthetic penicillins, which contributed to the colonization and proliferation of fungi.

The initial phase of colonization is adhesion, which is implemented through a variety of mechanisms for the recognition of host tissues by a pathogen (fungus). *Candida albicans* is able of binding to various substrates, such as mucosal (buccal, vaginal, dermal, and other) epitheliocytes, endotheliocytes, and inert surfaces (various polymers used in medical procedures). Adhesion in a macroorganism-microorganisms system depends on the external environment which, on the one hand, acts through the Candida and, on the other, affects indirectly through the host. Candida-dependent mechanisms include the surface hydrophobicity of the fungus, the type of culture medium, and growth conditions. The adhesive potential of the cells of a macroorganism is affected by the hormonal and immune status of the host. Attachment of Candida to host cells initiates colonization and the infection process. This concept is just the underlying idea of attempts at preventing the development of infections by blocking the adhesion of Candida to host tissues (see E. G. Zelenova, M. I. Zaslavskaya, E. V. Salina, and S. P. Rassanov, "Oral Microflora: Normality and Pathology. Textbook," Nizhni Novgorod: NGMA Publishing House, 2004, p. 121).

Xylitol is known to have a certain anti-adhesive potential against Candida fungi. The use in children aged 12 to 36 months of a gel comprising 10% xylitol for a period of 1 month was shown to have a positive effect on the microbiota composition of the tooth biofilm by normalizing the qualitative composition (speciation), and to result in the disappearance of Candida fungi (see E. V. Kirillova, V. N. Tsarev, L. P. Kiselnikova, and V. O. Artemova, Microbiological Monitoring of the Tooth Biofilm when Chlothexidine and Xylitol are Used in Complex Therapy of Dental Caries in Children of Early Ages," Stomatologiya Detskogo Vozrasta i Profilaktika, 2, 2009).

However, the use of toothpastes comprising 10% xylitol in children aged 6 to 12 years did not significantly change the content of Candida fungi in the mouth (see L. R. Sarap with colleages, AGMU, Barnaul, 2008, unpublished data).

Therefore, the invention uses water-soluble alginic acid salts for enhancing the efficacy of the xylitol-comprising preparations for the reason that they provide a prolonged antibacterial effect and are sorbents for circulating immune complexes (see L. K. Dobrodeeva and K. G. Dobrodeev, "Immunomodulators of Plant and Algal Origin: A Monograph," Arkhangelsk: Arkhangelsk State Technical University, 2008, pp. 238-239).

Example Gel Formulations and Preparation Thereof

The feasibility of embodying the prophylactic composition as a gel is illustrated by examples displayed in Table 1.

The gel formulation is prepared in the following manner.

The required amount of water is weighed in a measuring vessel; the water is poured to a mixer to which methylparaben, sorbitol, and xylitol are then added. The mixture is stirred for 20 min to obtain a clear solution.

A suspension of alginates and hydroxyethylcellulose in glycerol is prepared separately. This suspension is added to the above aqueous solution and stirred for 20 to 30 min to obtain a homogeneous gel.

Separately, polysorbate 20 is heated to a temperature of 40 to 45° C., a fragrance is added, and stirred for 10 min to obtain a homogeneous mixture. The resultant mixture is added to the gel, sodium lauryl sulfate is added, and stirred for 20-30 min to obtain a homogeneous mixture.

The gel prepared in this way is packed into tubes made of a polymeric material.

TABLE 1

| | Concentration, % by weight | | | | |
|---|---|---|---|---|---|
| Component | Example 1 | Example 2 | Example 3 | Example 4 | Example 5 |
| Glycerol | 30 | 15 | 10 | 6 | 3 |
| Sorbitol | — | 3 | 10 | 12 | 20 |
| Hydroxyethylcellulose | 0.5 | 0.8 | 1.0 | 1.5 | 1.8 |
| Xylitol | 0.6 | 2.0 | 6.0 | 10.0 | 8.0 |
| Potassium alginate | 1.5 | 0.5 | 0.8 | 0.5 | 0.2 |
| Sodium alginate | — | 0.5 | 0.2 | 0.1 | — |
| Polysorbate 20 | 1.0 | 0.8 | 0.6 | 0.8 | 1.2 |
| Sodium lauryl sulfate | 0.2 | 0.3 | 0.4 | — | — |
| Methylparaben | 0.05 | 0.08 | 0.15 | 0.2 | 0.3 |
| Fragrance | 0.06 | 0.10 | 0.12 | 0.18 | 0.22 |
| Water | up to 100% | up to 100% | up to 100% | up to 100% | up to 100% |

Example Toothpaste Formulations and Preparation Thereof

The feasibility of embodying the prophylactic composition as toothpaste is illustrated by examples displayed in Table 2.

The toothpaste is prepared in the following manner.

The required amount of glycerol is weighed, and xanthan gum and alginates are added thereto. The mixture is stirred to obtain a homogeneous mass.

The required amount of water is weighed in a dispenser, and the water is poured to a mixer to which sodium saccharinate, parabens, sorbitol, xylitol, sodium fluoride, sodium monatiorophosphate, and magnesium glycerophosphate are then added. The mixture is stirred to obtain a clear solution.

TABLE 2

| | Concentration, % by weight | | | | |
|---|---|---|---|---|---|
| Component | Example 1 | Example 2 | Example 3 | Example 4 | Example 5 |
| Glycerol | 19 | 20 | 25 | 15 | 5 |
| Sorbitol | — | — | — | 10 | 20 |
| Silica | 20 | 22 | 25 | 15 | 10 |
| Sodium bicarbonate | — | — | — | 8 | 15 |
| Xylitol | 2.0 | 5.0 | 10.0 | 12.0 | 18.0 |
| Xanthan gum | 0.2 | 0.5 | 0.8 | 1.2 | 1.5 |
| Potassium alginate | 1.1 | 0.8 | 0.4 | 0.2 | — |
| Sodium alginate | — | — | 0.4 | 0.1 | 0.2 |
| Magnesium glycerophosphate | 1.5 | 1.0 | 0.5 | — | — |
| Sodium monofluorophosphate | 1.0 | 0.8 | 0.6 | 0.2 | — |
| Sodium fluoride | — | — | — | 0.1 | 0.2 |
| Sodium lauryl sulfate | 1.0 | 1.2 | 1.4 | — | — |
| Alkylamidobetain | — | — | 0.5 | 1.0 | 1.5 |
| Methylparaben | 0.2 | 0.25 | 0.3 | 0.2 | 0.15 |
| Propylparaben | 0.06 | 0.08 | 0.1 | 0.12 | 0.15 |
| Sodium saccharinate | 0.05 | 0.08 | 0.12 | 0.22 | 0.30 |
| Fragrance | 0.4 | 0.6 | 1.2 | 1.8 | 1.0 |
| Water | up to 100% | up to 100% | up to 100% | up to 100% | up to 100% |

The resulting solution is added with a suspension of xanthan gum and alginates in glycerol and stirred to obtain a homogeneous mass. The formulation is degassed and stirred for 10 min to completely remove air from the mixture.

Following this, silica and then sodium bicarbonate are added, evacuated, and stirred for 30 to 40 min.

Then, the toothpaste is homogenized for 10 to 20 min by means of a homogenizer pump.

A fragrance and sodium lauryl sulfate (or alkylamidobetain) are added to the mixer and stirred for 20 to 30 min to obtain a homogeneous mass.

The toothpaste prepared in this way is packed into tubes made of a polymeric material.

Example Liquid Formulations and Preparation Thereof

The feasibility of embodying a prophylactic oral care composition as a liquid formulation is illustrated by examples shown below in Table 3.

TABLE 3

| | Concentration, % by weight | | | | |
|---|---|---|---|---|---|
| Component | Example 1 | Example 2 | Example 3 | Example 4 | Example 5 |
| Glycerol | 5 | 8 | 12 | 18 | 2.2 |
| Propylene glycol | 5 | 10 | 20 | — | — |

TABLE 3-continued

| Component | Example 1 | Example 2 | Example 3 | Example 4 | Example 5 |
|---|---|---|---|---|---|
| Xylitol | 1.0 | 5.0 | 8.0 | 10.0 | 3.0 |
| Potassium alginate | 0.5 | 0.3 | 0.2 | 0.1 | — |
| Sodium alginate | — | — | 0.1 | 0.2 | 0.3 |
| Polysorbate 20 | 0.8 | 0.6 | 0.5 | 1.0 | 1.2 |
| Sodium lauryl sulfate | 0.5 | 0.8 | 1.2 | — | — |
| Methylparaben | 0.24 | 0.18 | 0.12 | 0.08 | 0.05 |
| Stevioside | 0.008 | 0.01 | 0.08 | 0.12 | 0.18 |
| Fragrance | 0.1 | 0.15 | 0.22 | 0.25 | 0.32 |
| Water | up to 100% | up to 100% | up to 100% | up to 100% | up to 100% |

The required amount of water is heated in a dispenser to 4045° C. and poured to a mixer to which stevioside and xylitol are then added. The mixture is stirred for 10 to 15 min to obtain a clear solution.

Methylparaben is dissolved in propylene glycol in a separate vessel under stirring; then this solution is added to the main mixer and stirred to obtain a clear solution.

Glycerol is charged into a separate vessel, and alginate is added under stirring. Then, the suspension obtained in this way is added to the main solution.

The mixture is stirred to obtain a clear solution.

Polysorbate 20 is separately heated to a temperature of 40 to 45° C., a fragrance is added, stirred for 10 min to obtain a homogeneous mixture, and then added to the mixture obtained at the preceding step.

The composition is stirred for 20 min to obtain a clear or slightly opalescent solution. Sodium lauryl sulfate is added; the solution is stirred for 20 min and dispensed into plastic bottles.

Example Cosmetic Emulsion Cream Formulations and Preparation Thereof

The feasibility of embodying the prophylactic composition as a cosmetic emulsion cream is illustrated by examples displayed in Table 4.

The required amount of water is poured into a mixer to which sorbitol, xylitol, and sodium benzoate are then added. Into the vortex formed by stirrer rotation, alginate is slowly added. The mixture is heated to a temperature of 55 to 60° C. and stirred for 20-30 min to obtain a homogeneous gel.

Olive oil, jojoba oil, dimethicone, stearic acid, caprylic triglycerides, glyceryl monostearate, glyceryl oleate citrate, and C14-16 fatty alcohols are placed into a separate vessel, and melted at 55-60° C. The oil phase is poured to the aqueous phase under stirring, and emulsified for 15-20 min under stirring and heating at 55-60° C. The emulsion is cooled to a temperature of 40 to 50° C., and a fragrance is added under stirring.

Following this, the cream is homogenized for 1-2 min at a temperature of 40 to 50° C. at a homogenizer speed of 5000 to 7000 rpm. The ready for use cream is packed into polymer tubes or jars.

TABLE 4

| Component | Example 1 | Example 2 | Example 3 | Example 4 | Example 5 |
|---|---|---|---|---|---|
| Sorbitol | 3 | 5 | 6 | 8 | 5 |
| Olive oil | 10 | — | 8 | 6 | 5 |
| Jojoba oil | — | 3.5 | — | — | — |
| Xybtol | 5 | 8 | 10 | 12 | 10 |
| Potassium alginate | 0.5 | 1 | 0.4 | 0.2 | 0.5 |
| Sodium alginate | — | — | 0.4 | 0.2 | — |
| Glyceryl monostearate | 1.5 | 1.3 | 0.84 | 1.05 | 1.65 |
| Glyceryl oleate citrate | 0.5 | 0.35 | 1.08 | 1 | 1.5 |
| Caprylic triglycerides | 0.5 | 0.35 | 1.08 | 1 | 1.5 |
| Stearic acid | — | — | 1 | 1 | 0.8 |
| C14-C16 fatty alcohols | — | — | 2 | 2 | 1.5 |
| Dimethicone | — | — | — | — | 1 |
| Sodium benzoate | 0.3 | 0.2 | 0.1 | 0.05 | 0.12 |
| Fragrance | 0.2 | 0.3 | 0.4 | 0.25 | 0.15 |
| Water | up to 100% | up to 100% | up to 100% | up to 100% | up to 100% |

Evaluation of Efficacy

The efficacy of the prophylactic composition for the prevention of candidiasis is illustrated with the use of toothpaste prepared according to the invention.

The efficacy was verified by a laboratory method as the degree of destruction of the monolayer of skin-muscle human embryo fibroblasts, that is, as the degree of reduction of the toxic effect.

The test microorganism culture was a laboratory *Candida albicans* strain; the microbial load was 106-7 CFU/g. The exposure time was 4 hours.

Distilled water served as the blank.

The toothpaste prepared according to the invention and the placebo toothpaste had the formulations as shown in Table 5.

TABLE 5

| Component | Placebo toothpaste | Toothpaste according to the invention |
|---|---|---|
| Glycerol | 20 | 20 |
| Xanthan gum | 1.2 | 0.2 |
| Potassium alginate | — | 1.25 |
| Xylitol | — | 10 |
| Silica | 15 | 15 |
| Alkyiamidobetain | 1.2 | 1.2 |
| Sodium saccharinate | 0.2 | 0.2 |
| Sodium benzoate | 0.3 | 0.3 |
| Fragrance | 1 | 1 |
| Water | up to 100% | up to 100% |

After toothpaste samples were prepared, they were dispersed in distilled water.

The following results were obtained:

(a) With the blank, the monolayer was destroyed completely (by 100%); 20 *Candida albicans* cells were detected per fibroblast cell;

(b) With the placebo sample, the monolayer was destroyed by 75%; the residue was 12 to 14 *Candida albicans* cells per fibroblast cell;

(c) With the toothpaste sample prepared according to the invention, the monolayer was destroyed by 10%; the residue was 4 to 5 *Candida albicans* cells per fibroblast cell.

It follows that a highly efficient composition for preventing candidiases has been prepared on the basis of xylitol and water-soluble sodium and/or potassium salts of alginic acid, which are safe for humans, specifically, for babies. This composition can be used by people who belong to the group of risk, namely: sufferers of diabetes mellitus, people with blood diseases, immune deficiency, or other severe pathologies; patents subjected to hormone therapy, antibiotic therapy, or chemotherapy; babies and pregnant women; and people using dentures.

The active components of the composition are available throughout the world and allowed for use as dietary supplements.

According to the invention, the composition for preventing candidiases may be prepared in the form of a gel for oral hygiene or for application to the human skin or mucosal surfaces, in the form of toothpaste, in the form of a cream for application to the skin, or a liquid formulation for mouth rinsing or washing the human mucosal surfaces or skin and/or for application to the skin.

The invention claimed is:

1. In a method for prophylactic treatment of a patient who is subject to an increased risk of a fungal yeast infection caused by *Candida albicans*, the method comprising administering to a mucosal surface of the patient a composition comprising xylitol in an amount effective for inhibiting the infection, the improvement comprising including an alginate in an amount effective to enhance an antifungal effect of the composition in inhibiting the infection as compared with the composition without the alginate, wherein the composition consists of active components and inert components, and the active components consist of (a) xylitol and (b) sodium alginate, potassium alginate or both, wherein the alginate is present in the composition in an amount of 1 to 2 wt. % and the xylitol is present in the composition in an amount of 10% by weight.

2. The method according to claim 1, wherein the composition is a gel, said get comprising inert components comprising, in percent by weight:
moistening component 5-70
gelling component 0.5-3.0
surfactant 0.3-3.0
fragrance 0.05-0.3
preservative 0.01-0.5 and
water up to 100,
wherein the moistening component comprises one or more components selected from the group consisting of: sorbitol, glycerol, polyethylene glycol, and propylene glycol, and
wherein the surfactant comprises one or more components selected from the group consisting of: sodium lauryl sulfate, sodium lauryl sarcosinate, glyceryl stearate citrate, glyceryl oleate citrate, potassium cetyl phosphate, cetearyl alcohol, glyceryl monostearate, hydrogenated castor oil, polysorbate 20, cetearyl glycoside, sorbitan isostearate, and alkylamidobetain.

3. The method according to claim 1, wherein the composition is toothpaste, said toothpaste comprising inert components comprising, in percent by weight:
abrasive component 10-30
moistening component 5-70
gelling component 0.5-3.0
anticaries component 0.1-2.5
surfactant-0.5-3.0
fragrance 0.3-2.0
sweetener 0.01-0.3 and
water up to 100,
wherein the moistening component comprises one or more components selected from the group consisting of: sorbitol, glycerol, polyethylene glycol, and propylene glycol, and
wherein the surfactant comprises one or more components selected from the group consisting of: sodium lauryl sulfate, sodium lauryl sarcosinate, glyceryl stearate citrate, glyceryl oleate citrate, potassium cetyl phosphate, cetearyl alcohol, glyceryl monostearate, hydrogenated castor oil, polysorbate 20, cetearyl glycoside, sorbitan isostearate, and alkylamidobetain.

4. The method according to claim 1, wherein the composition is a cosmetic emulsion cream, said cream comprising inert components comprising, in percent by weight:
moistening component 0.2-10
surfactant 0.5-4.0
emollient 0.5-30
structuring agent 1.0-3.0
fragrance 0.01-0.5
preservative 0.01-0.5 and
water up to 100,
wherein the moistening component comprises one or more components selected from the group consisting of: sorbitol, glycerol, polyethylene glycol, and propylene glycol, and
wherein the surfactant comprises one or more components selected from the group consisting of: sodium lauryl sulfate, sodium lauryl sarcosinate, glyceryl stearate citrate, glyceryl oleate citrate, potassium cetyl phosphate, cetearyl alcohol, glyceryl monostearate, hydrogenated castor oil, polysorbate 20, cetearyl glycoside, sorbitan isostearate, and alkylamidobetain.

5. The method according to claim 1, wherein the composition is a liquid formulation, said formulation comprising inert components comprising, in percent by weight:
moistening component 3.0-70
surfactant 0.5-3.0
fragrance 0.01-0.5
sweetener 0.005-0.2
preservative-0.01-0.5 and
water up to 100,
wherein the moistening component comprises one or more components selected from the group consisting of: sorbitol, glycerol, polyethylene glycol, and propylene glycol, and
wherein the surfactant comprises one or more components selected from the group consisting of: sodium lauryl sulfate, sodium lauryl sarcosinate, glyceryl stearate citrate, glyceryl oleate citrate, potassium cetyl phosphate, cetearyl alcohol, glyceryl monostearate, hydrogenated castor oil, polysorbate 20, cetearyl glycoside, sorbitan isostearate, and alkylamidobetain.

6. The method according to claim 3, wherein the abrasive component comprises one or more components selected from the group consisting of: silica, polymethacrylate, calcium pyrophosphate, and sodium bicarbonate.

7. The method according to claim 2, wherein the gelling component comprises one or more components selected from the group consisting of: hydroxyethylcellulose, xanthan gum, guar gum, and carboxymethylcellulose.

8. The method according to claim 4, wherein the emollient comprises one or more components selected from the group consisting of: caprylic triglycerides, isopropyl myristate, cetearylethyl hexanoate, olive oil, avocado oil, jojoba oil, Shea Butter, wheat germ oil, sunflower seed oil, dimethicone, and cyclomethicone.

9. The method according to claim 4, wherein the structuring agent comprises one or more components selected from the group consisting of C14-16 fatty alcohols, stearic acid, and palmitic acid.

10. The method according to claim 3, wherein the anti-caries component comprises one or more components selected from the group consisting of: sodium fluoride, potassium fluoride, sodium monofluorophosphate, potassium monofluorophosphate, and magnesium glycerophosphate.

11. The method according to claim 3, wherein the sweetener comprises one or more components selected from the group consisting of: sodium saccharinate, potassium aspartame, stevioside, and potassium or sodium glycyrrhizate.

12. The method according to claim 1, wherein the patient suffers from a disease that makes the patient more susceptible to the infection, the disease being selected from the group consisting of diabetes mellitus, immune deficiency and a blood disease.

13. The method according to claim 1, wherein the patient is undergoing a treatment that makes the patient more susceptible to the infection, the treatment being selected from the group consisting of hormone therapy, antibiotic therapy and chemotherapy.

14. The method according to claim 1, wherein the patient is a baby, a pregnant woman or a person using dentures.

15. The method according to claim 1, wherein the alginate is present in the composition in an amount of 2% by weight.

16. The method according to claim 1, wherein the alginate is present in the composition in an amount of about 1.5% by weight.

17. The method according to claim 1, wherein the alginate is present in the composition in an amount of about 1% by weight.

18. The method according to claim 1, wherein the alginate is present in the composition in an amount of about 1.25% by weight.

* * * * *